(12) United States Patent
Masud et al.

(10) Patent No.: US 12,346,547 B2
(45) Date of Patent: Jul. 1, 2025

(54) ON-DEMAND MANUFACTURING FOR MEDICAL TAPES

(71) Applicant: 3M INNOVATIVE PROPERTIES COMPANY, St. Paul, MN (US)

(72) Inventors: Md Abdulla Al Masud, St. Paul, MN (US); Lindsey L. Hines, Stillwater, MN (US); Chin-Yee Ng, Oakdale, MN (US); Jia Hu, Mounds View, MN (US); Perry S. Dotterman, Maplewood, MN (US); Bryan T. Whiting, St. Paul, MN (US); Audrey A. Sherman, Woodbury, MN (US); Taylor J. Kobe, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 18/717,723

(22) PCT Filed: Dec. 29, 2022

(86) PCT No.: PCT/IB2022/062885
§ 371 (c)(1),
(2) Date: Jun. 7, 2024

(87) PCT Pub. No.: WO2023/126877
PCT Pub. Date: Jul. 6, 2023

(65) Prior Publication Data
US 2025/0053288 A1    Feb. 13, 2025

Related U.S. Application Data

(60) Provisional application No. 63/266,184, filed on Dec. 30, 2021.

(51) Int. Cl.
*G06F 3/04847* (2022.01)
*A61F 13/02* (2006.01)

(52) U.S. Cl.
CPC ...... *G06F 3/04847* (2013.01); *A61F 13/0283* (2013.01)

(58) Field of Classification Search
CPC .................. A61F 13/0283; G06F 3/04847
See application file for complete search history.

(56) References Cited

U.S. PATENT DOCUMENTS

| 6,812,170 B1 | 11/2004 | Himmelsbach |
| 12,115,772 B2 * | 10/2024 | Roeder ............... B41F 16/0086 |

(Continued)

FOREIGN PATENT DOCUMENTS

| CN | 105731136 B | 4/2017 |
| CN | 110664541 A | 1/2020 |

(Continued)

OTHER PUBLICATIONS

International Search Report for PCT International Application No. PCT/IB2022/062885, mailed on Apr. 6, 2023, 3 pages.

(Continued)

*Primary Examiner* — Vincent H Tran
(74) *Attorney, Agent, or Firm* — Yufeng Dong; Sriram Srinivasan (57) ABSTRACT

Systems and methods for customizing medical tapes from a roll stock at customer use sites are provided. The system includes a tape converting machine where an adhesion modification mechanism is configured to modify adhesion properties of the tape from the roll stock, automatically or based on received customization instructions.

16 Claims, 9 Drawing Sheets

(56) References Cited

U.S. PATENT DOCUMENTS

| | | | | |
|---|---|---|---|---|
| 2009/0076905 | A1* | 3/2009 | Kraft | G06Q 30/02 705/14.25 |
| 2010/0046010 | A1* | 2/2010 | Bauer | B44F 9/02 358/1.9 |
| 2013/0191211 | A1* | 7/2013 | Nichols | G06Q 30/02 705/14.49 |
| 2019/0085217 | A1* | 3/2019 | Lo | C09J 7/35 |
| 2019/0160700 | A1* | 5/2019 | Witkin | B41J 11/70 |
| 2020/0226301 | A1* | 7/2020 | Siu | G06F 30/00 |
| 2020/0283171 | A1* | 9/2020 | Holmes | G01N 25/72 |
| 2021/0067658 | A1* | 3/2021 | Xu | B41J 3/4078 |
| 2021/0326312 | A1* | 10/2021 | White | G06F 16/248 |

FOREIGN PATENT DOCUMENTS

| | | |
|---|---|---|
| CN | 113509626 A | 10/2021 |
| CN | 112770704 B | 8/2023 |
| DE | 102006018499 A1 | 8/2007 |
| EP | 0855892 A1 | 8/1998 |
| EP | 0827453 B1 | 12/1999 |
| EP | 0722586 B1 | 12/2001 |
| EP | 1542631 A1 | 6/2005 |
| EP | 2337473 B1 | 4/2015 |
| EP | 3036701 A1 | 6/2016 |
| EP | 2882392 B1 | 3/2019 |
| EP | 3080351 B1 | 11/2019 |
| JP | 3150309 U * | 5/2009 |
| JP | 2016504066 A | 2/2016 |
| JP | 2016043126 A | 4/2016 |
| KR | 20170036577 A | 4/2017 |
| WO | 03094811 W | 11/2003 |
| WO | 2014078518 A1 | 5/2014 |
| WO | 2015184088 A1 | 12/2015 |

OTHER PUBLICATIONS

Kuplicki, "Navigating Reimbursement for Wound Care Dressings", Wound Source, URL: <https://www.woundsource.com/blog/navigating-reimbursement-wound-care-dressings>, 2015, pp. 1-10.

* cited by examiner

ON-DEMAND MANUFACTURING FOR MEDICAL TAPES

CROSS-REFERENCE TO RELATED APPLICATIONS

This application is a national stage filing under 35 U.S.C. § 371 of International Application PCT/IB2022/062885, filed 29 Dec. 2022, which claims the benefit of Provisional U.S. Patent Application No. 63/266,184, filed 30 Dec. 2021, the entire disclosure of each of which is incorporated herein by reference.

BACKGROUND

Medical tapes and dressings are made in many shapes and sizes to accommodate different user needs. Because every patient's case differs from person to person, clinicians and physicians need to take on any number of variances as they attend patients' needs.

SUMMARY

There is a desire to customize properties of medical tapes at decentralized manufacturing sites, e.g., at or near customer use sites. The present disclosure provides on-demand manufacturing systems and methods for medical tapes or dressings.

In one aspect, the present disclosure describes a system of making a customized medical tape. The system includes one or more compact tape converting machines having a volume no greater than 5 $m^3$, at least one of the tape converting machines including a roll of tape, an adhesion modification mechanism configured to modify adhesion properties of the tape, and a communication device; and a computing device including a second communication device communicatively connected to the communication device of the at least one tape converting machine, one or more computer processors, and a non-transitory, tangible computer-readable memory including instructions that when executed by the one or more computer processors cause the computer processors to: generate for display a user interface that allows a user to input instructions to modify the adhesion properties of the tape; and analyze the instructions to determine machine run parameters for the one or more tape converting machines.

In another aspect, the present disclosure describes a method of customizing a medical tape. The method includes accessing to one or more compact tape converting machines having a volume no greater than 5 $m^3$, at least one of the tape converting machines including a roll of tape, an adhesion modification mechanism configured to modify adhesion properties of the tape, and a communication device; and accessing to a computing device including a second communication device communicatively connected to the communication device of the at least one tape converting machine, one or more computer processors, and a non-transitory, tangible computer-readable memory comprising instructions that when executed by the one or more computer processors cause the computer processors to: generate for display a user interface that allows a user to input instructions to modify the adhesion properties of the tape; and analyze the instructions to determine machine run parameters for the one or more tape converting machines.

Various unexpected results and advantages are obtained in exemplary embodiments of the disclosure. Advantages of exemplary embodiments of the present disclosure include, for example, the ability to generate specific regions of low and strong adhesion allowing unique capabilities, e.g., strongly bonded endotracheal tubes with gentle skin attachment in one piece of tape. Gradually or rapidly transitioning adhesion regions can ease (or render more difficult to accidental) removal of the adhesive tape or dressing. The on-demand flexibility also relieves the requirement to store a large inventory of different strength tapes, while still providing the current level of adhesion for specific patient needs. This supports efforts to prevent MARSI (Medical Adhesive Related Skin Injury) by always having the correct level of adhesion for the specific application. As a complete system, effort required for ordering, stocking, shipping, receiving, transportation and the associated time to do so can be significantly reduced or eliminated. Connectivity to cloud computing environment allows retrieval of the most up to date parameters/testing/modeling results to optimize desired output while also allowing the ability to track and predict future patient and hospital or clinic needs.

Various aspects and advantages of exemplary embodiments of the disclosure have been summarized. The above Summary is not intended to describe each illustrated embodiment or every implementation of the present certain exemplary embodiments of the present disclosure. The Drawings and the Detailed Description that follow more particularly exemplify certain preferred embodiments using the principles disclosed herein.

BRIEF DESCRIPTION OF THE DRAWINGS

The disclosure may be more completely understood in consideration of the following detailed description of various embodiments of the disclosure in connection with the accompanying figures, in which.

In the drawings, like reference numerals indicate like elements. While the above-identified drawing, which may not be drawn to scale, sets forth various embodiments of the present disclosure, other embodiments are also contemplated, as noted in the Detailed Description. In all cases, this disclosure describes the presently disclosed disclosure by way of representation of exemplary embodiments and not by express limitations. It should be understood that numerous other modifications and embodiments can be devised by those skilled in the art, which fall within the scope and spirit of this disclosure.

DETAILED DESCRIPTION

The present disclosure provides systems and methods for customizing medical tapes and dressings. The customization occurs at the edge, e.g., at or close to the customer use site, where the suitable and precise adhesion strength in the whole area or partially selected area(s) of a tape or dressing can be produced exactly where and when it is needed and can be changed as the wound and patient needs progress.

Figure 1:
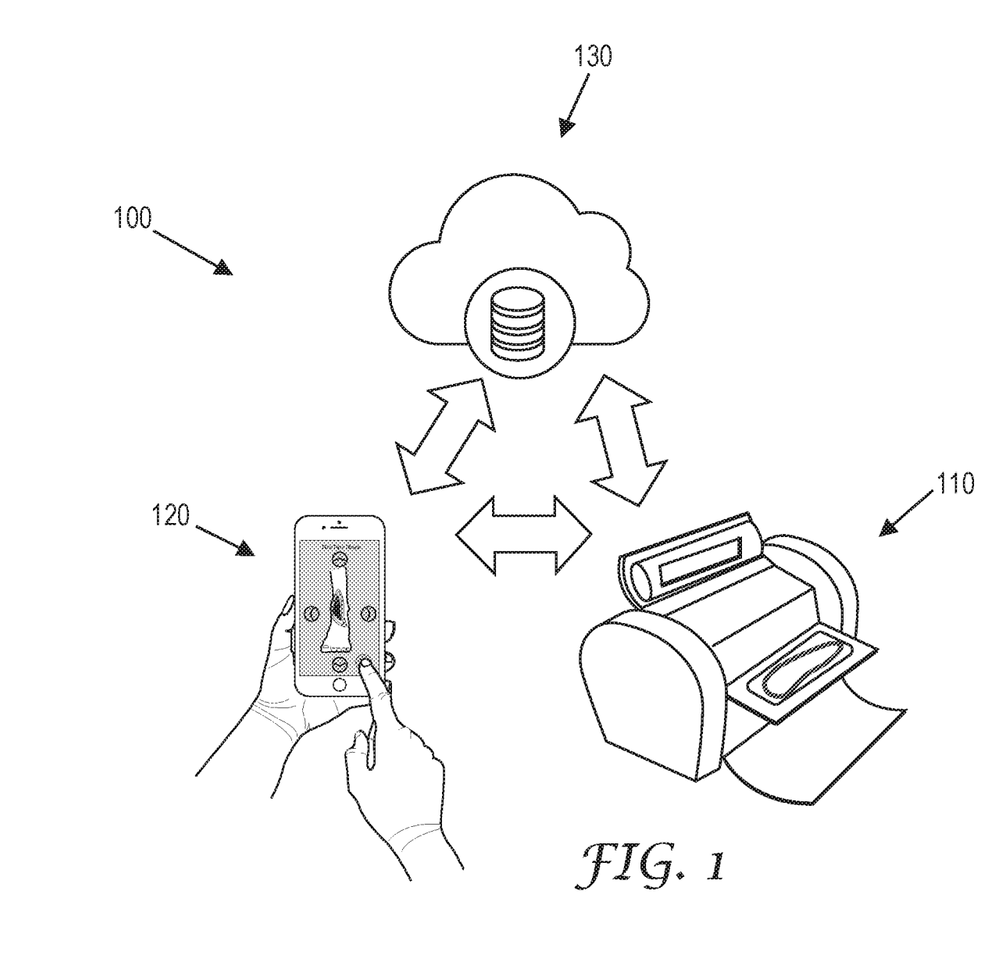
FIG. 1 is a schematic diagram of a medical tape customization system, according to one embodiment.

FIG. 1 is a schematic diagram illustrating an exemplary tape customization system 100 in which one or more compact tape converting machines 110 are used to modify tape adhesive properties supplied by a roll stock inside the compact tape converting machines 110. Customized tape modifications are controlled by a tape converting management system, such as a management system 6 shown in FIG. 2. The compact tape converting machines 110 each have a compact size with a volume, for example, no greater than 5 $m^3$, no greater than 3 $m^3$, or no greater than 2 $m^3$. The compact size allows the tape converting machines 110 to be a portable or desktop machine that can be easily distributed and installed at decentralized manufacturing sites, at or close to customer use sites such as, for example, points of care, distribution centers, stores, etc. At least one of the tape converting machines 110 includes roll stocks of adhesive tape. The adhesive tape has an adhesive surface supported by a backing material and may be stored as a roll stock inside the machine 110, where a desired amount can be dispensed at a given time to prepare customized medical tapes or dressings to address patients' needs. An adhesion modification mechanism of the tape converting machines 110 is configured to modify the adhesion properties of the tape for the customized medical tapes or dressings. The converting machines 110 with a small footprint can perform the flexible adhesion modification on roll stocks, and process the tapes to output the modified film for ease of handling or storage.

The tape customization system 100 further provides a custom interface 120 that allows customers or operators to enter information of customization and orders, including adhesion requirements at a high or low level for the customized tapes. The custom interface 120 can be displayed, for example, by a mobile device to the user. Various algorithms can be used to interpret user needs to generate adhesion patterns for a customized tape or dressing, and the corresponding machine run parameters for the tape converting machine. The medical tape customization system 100 may further include one or more computing devices to implement the algorithms.

The computing devices of the tape customization system 100 may further include a communication device communicatively connected to other components or devices of the tape converting machines 110. The computing devices include one or more computer processors, and a non-transitory, tangible computer-readable memory including instructions that when executed by the one or more computer processors cause the computer processors to generate for display a user interface that allows a user to input instructions to modify the adhesive surface of the tape, and analyze the instructions to determine machine run parameters for the one or more tape converting machines 110. It is to be understood that the one or more computing devices can be physically located at any desired computer system resources such as, for example, a cloud computing environment, a mobile device, a local/remote computer, etc.

In the depicted embodiment of FIG. 1, a cloud computing environment 130 is provided for data processing, communication to devices or components of the system 100, as well as communication to outside the system for various tasks including placing order of supplies, bills and communicating remotely with customers, system maintenance, etc. The tape converting machines 110 may include a communication device communicatively connected to the cloud computing environment 130 and other devices or components of the system 100 such as a mobile device displaying the user interface 120.

Figure 2:
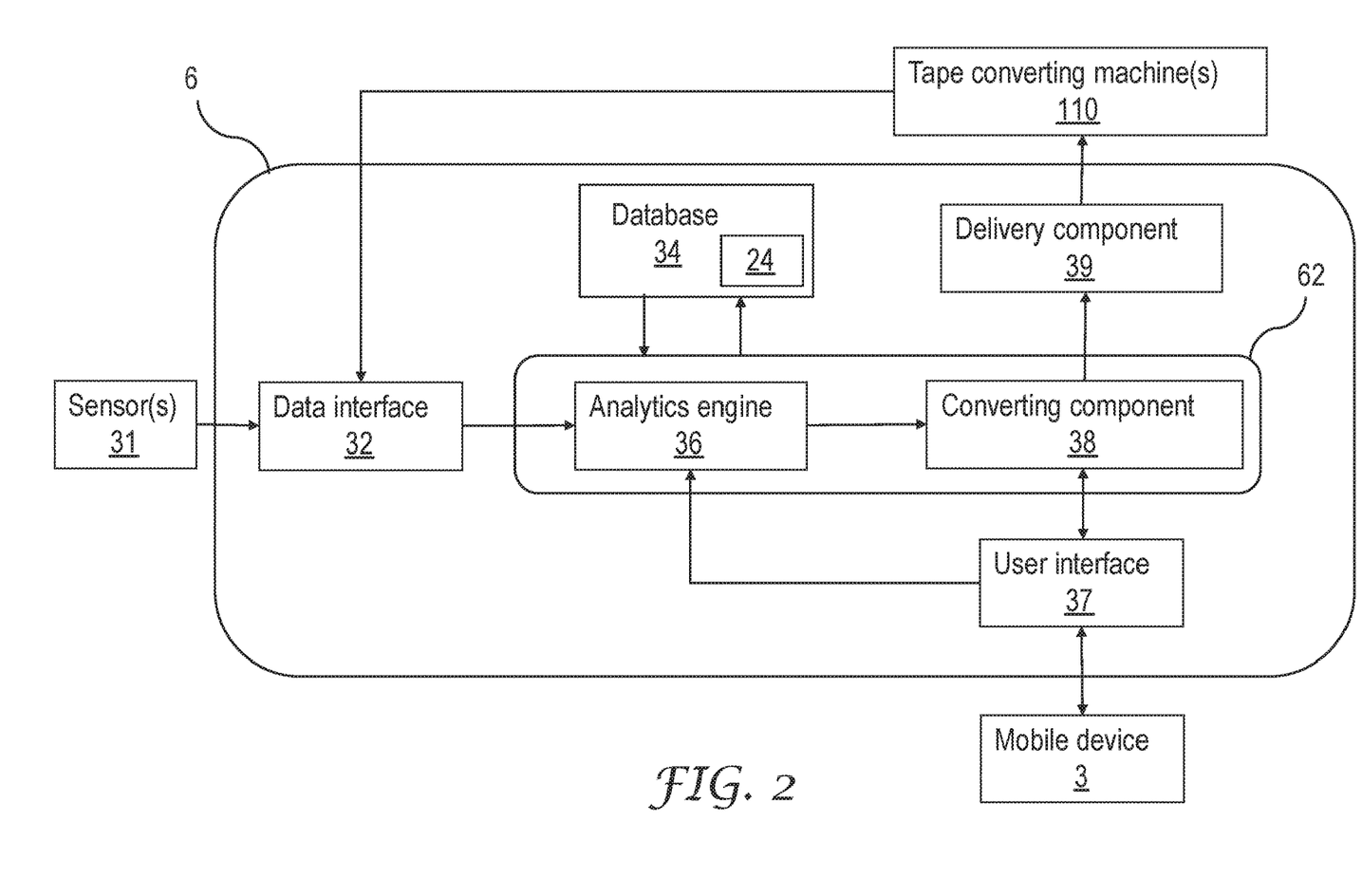
FIG. 2 is a block diagram illustrating a tape converting management system, according to one embodiment.

FIG. 2 is a block diagram illustrating a method of using a tape converting management system 6 to manage or control the modification and converting a roll stock of tape into customized tapes, according to one embodiment. The system 6 may be a cloud-based system having an analytics engine configured to process streams of incoming usage data from a user interface, various sensors, various tape converting machines, or a database storing data related to the user or the tape modification. In some embodiments, the management system 6 can be hosted as cloud-based platform capable of supporting multiple, distinct tape converting machines at different locations. The analytics engine of the system 6 can apply the streams of incoming usage data to determine how to modify or convert the tapes from the roll stocks at different locations to address the customization and order at the different locations.

The system 6 includes a data interface component 32 configured to receive imaging data from various vision or imaging sensors 31. For example, the vision or imaging sensors can scan a wound bed of a patient to provide imaging data to a vision system to process the data to obtain wound information such as, for example, the stage of wound healing. The wound information can be sent to the analytics engine 36 via the data interface component 32. The data interface component 32 may also receive data from the tape converting machines 110, for example, regarding the status of the tape converting machines 110 including, the current machine run parameters, the supply roll stock status, etc.

The system 6 further includes an intelligent edge manufacturing assistant 62 including the analytics engine 36 and a tape modification/converting component 38, which can provide guidance to a user (e.g., a nurse or a healthcare provide) and determine machine run parameters for the tape converting machines 110. The analytics engine 36 can assess patient information or variables from the data interface component 32 along with other information from the database component 34 to determine requirements for manufacturing the tapes. The database component 34 may store information including, for example, a pattern or design library for tapes or dressings such as pre-defined schematic drawings or designs for adhesion modification or cutting patterns after the modification. The database component 34 may further store information related to pre-set policies or rules, which can be, for example, mapping information between the patient's wound status and the suitable adhesion level or pattern of the customized tape or dressing.

The tape modification/converting component 38 receives instructions from the analytics engine 36 and determine suitable machine run parameters for the tape converting machines 110. For example, in some embodiments, the analytics engine 36 can assess the patient information from the data interface 32 and the related pre-set rule from the database component 34 to determine adhesion requirements at a high or low level. For example, the analytics engine 36 can determine in the whole area or partially selected area(s) of a tape or dressing with a low or strong adhesion allowing unique capabilities, e.g., strongly bonded to endotracheal/IV/procedure tubes, bonds gently to skin on a single strip of tape, etc. Based on the assigned level of adhesion, the tape converting component 38 can determine appropriate machine run parameters such as, for example, suitable means of adhesion modifications to satisfy the adhesion requirements, etc.

In some embodiments, the intelligent edge manufacturing assistant 62 can directly deliver the determined machine run parameters to the tape converting/modification machines 110 via a delivery component 39. In some embodiments, the intelligent edge manufacturing assistant 62 may present the determined adhesion requirements and tape patterns to a user via the user interface 37, for example, displayed by a mobile device 3. The user may confirm, reject, or modify the automated design and send the feedback to the intelligent edge manufacturing assistant 62. The intelligent edge manufacturing assistant 62 may assess the feedback from the user and further modify the design of tape modification based on the user's feedback.

In some embodiments, the intelligent edge manufacturing assistant 62 can implement a machine learning process to determine adhesion requirements for tape modification and patterns to be cut from the tape after the adhesion modification. The machine learning process may use any suitable algorithm or model with the trained algorithms or models stored in the database component 34. For example, user data such as previous user selections can be used to inform and improve future suggestions. Existing models and experimental data can be used to train models to create outputs suitable to the unique and varied shapes and profiles for each wound variation.

In some embodiments, the intelligent edge manufacturing assistant 62 can automatically process streams of incoming usage data from the data interface 32 and the database 34 to generate automated designs for tape modification and patterns. The generated designs may include various modification configurations including, for example, adhesion levels, adhesion patterns, dressing patterns, etc. The automated designs can be present to the user via the user interface 37. In addition, the intelligent edge manufacturing assistant 62 may generate a query to present to the user via the user interface 37, and ask for the user's input to further clarify the user's needs regarding the tape modification.

Figure 3:
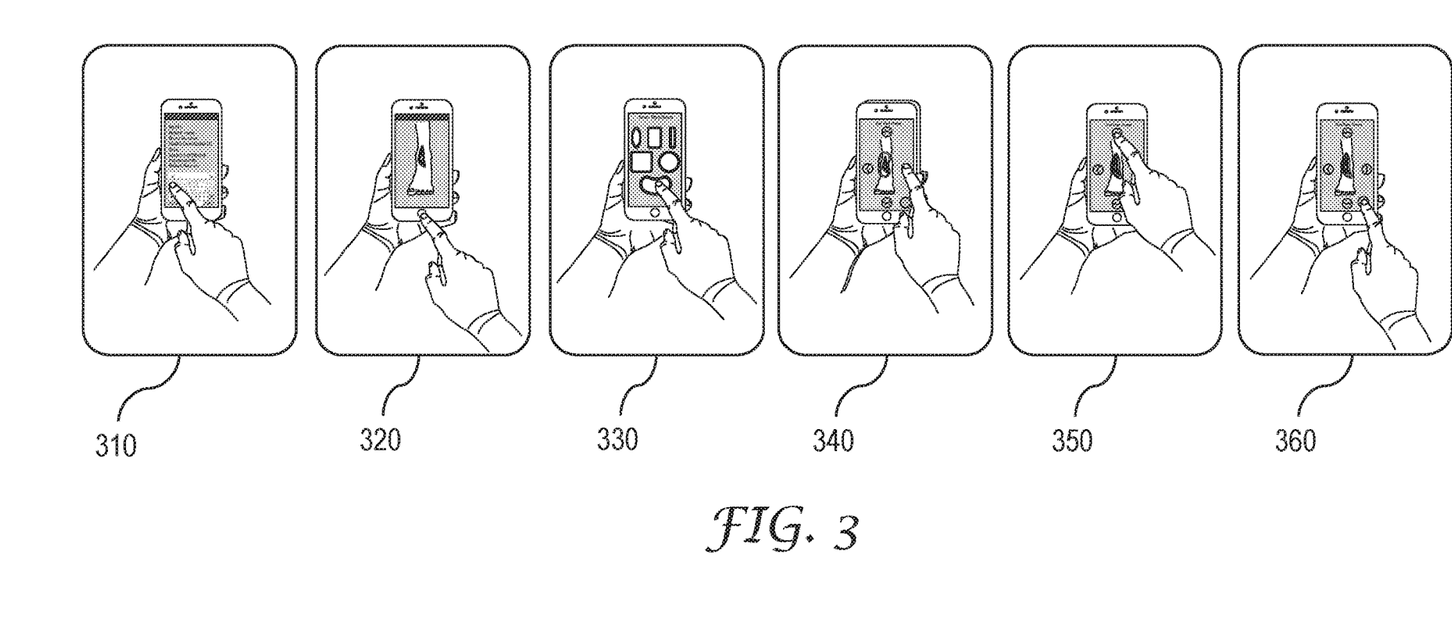
FIG. 3 illustrates various user interfaces of a tape converting management system, according to some embodiments.

FIG. 3 illustrates various user interfaces on a mobile device to interact with a user. In 310, the user interface instructs the user to provide user data (e.g., scan a wristband) and receives the user data to confirm particulars. In 320, the user interface instructs the user to take wound images, receives the image data, and presents analyzing results (e.g., a scale reference for the wound) to the user. In 330, the user interface instructs the user to select a desired output shape for the customized medical tape, and receives the user's input. In 340, the user interface instructs the user to select a size shape for the customized medical tape, and receives the user's input. In 350, the user interface presents a preview of the bandage on site, and invites the user's confirmation or rejection. In 360, the user interface instructs the user to submit an order to an edge manufacturing machine, and receives the user's input.

Figure 4:
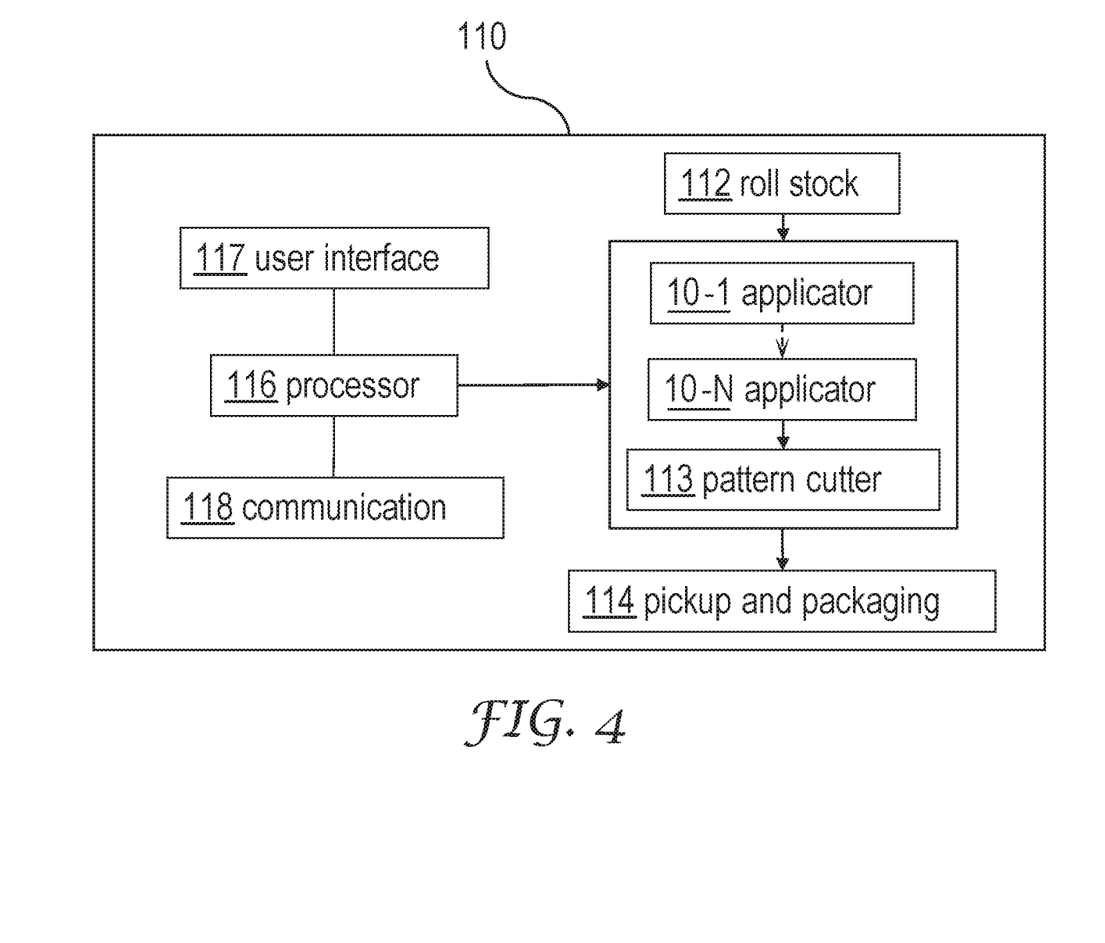
FIG. 4 is a block diagram of a tape converting machine, according to one embodiment.

FIG. 4 is a block diagram of a tape converting machine or tape manufacturing core 110, according to one embodiment. The tape converting machine or tape manufacturing core 110 is controlled via the tape converting management system 6 of FIG. 2 to modify or convert a tape from the roll stock 112 to a customized medical tape with desired adhesion level, adhesion pattern, tape or dressing pattern, shapes, or sizes. The converting process starts with a supply tape of roll stock 112 which may include an adhesive tape of certain properties of adhesion made in mass production. The tape passes through a series of adhesion modification mechanisms or applicators 10-1 . . . 10-N that modify the tape according to the user's demand, including, for example, adhesion properties, shapes (2D), forms (3D), colors, printing information or graphics, as well as desired packaging of each or a few pieces of the custom tape for picking up, storage and transportation via the pickup and packaging mechanism 114 before usage.

Various digitally-controlled applicators can be used to modify characteristics or properties of adhesion on the supply roll-stock tape 112. In some embodiments, one or more of the applicators may apply an adhesion surface modifier that can interact directly on the side of adhesive coating on the tape. The interaction of the modifier with the adhesive surface can be physical, chemical, optical, acoustic, etc. Suitable applicators can be, for example, inkjet printhead. UV light, laser, spray jet. 3D printing, etc. The modifier may render the tape adhesive surface partially or completely non-adhesive.

In some embodiments, the surface adhesive modifier may include a second adhesive having a different adhesion property than the adhesive surface of the tape. The applicator may further include a curing station configured to cure the second adhesive that is applied on the adhesive surface of the tape in a desired pattern. In some embodiments, the second adhesive can be applied on the adhesive surface of the tape by laminating a second adhesive tape onto the tape. Exemplary adhesive materials include acrylic, silicone, or rubber depending upon the application.

In some embodiments, the surface adhesive property of the tape can be altered by radiation, e.g., from an electromagnetic energy source or a thermal source.

In some embodiments, the surface adhesive modifier may include a powder material to be applied onto the adhesive surface of the tape. Exemplary powder material may include talc, povidone iodine, zinc oxide, etc.

In some embodiments, the surface adhesive modifier may include a phase changed material such as, for example, a wax which can be applied via printing a pattern over the adhesive surface of the tape.

In some embodiments, the surface adhesive modifier may include a reactive liquid such as, for example, acetone. In some embodiments, the surface adhesive modifier may include a non-reactive liquid such as, for example, water.

In some embodiments, one or more of the applicators can be applied to the backing layer of the tape to modify the surface adhesion properties of the tape. For example, the applicator may generate a structured surface (e.g., a non-flat surface) on the backing layer where adhesive material can be selectively applied. For example, the backing layer may have indents that influence which areas the adhesive can reside. The applicator may modify the backing layer to have a patterned, varying stiffness. The applicator may modify the backing layer such that adhesives selectively adhere to specified areas of the adhesive surface. The applicator may generate a chemical migration through the backing and adhesive to modify the adhesion properties of the tape. The applicator may apply a thermal radiation to the backing layer to thermally induce backing material property change.

In some embodiments, one or more of the applicators may include various cutters to cut a pattern of through holes in the tape. Suitable cutters may include, for example, a laser, a blade, a die, etc. The pattern of through holes may reduce the effective adhesive area of the tape to a level as desired by the user.

In some embodiments, a pattern cutter is provided downstream of the adhesion modification mechanism, configured to cut out a customized shape from the tape. Various cutters, for example, a laser, a blade, a die, etc. can be used to cutout overall tape shape to allow better attachment, for example, to moving joints, 3D shape, and healthy skin around wounded area.

In some embodiments, a pickup and packaging mechanism can be provided downstream of the pattern cutter, configured to pick up the customized shape. The pickup and packaging mechanism may include a cylinder and a vacuum plate to adhere to the customized shape.

The system of the edge manufacturing core 110 for custom tapes can also include a pattern cutter 113 that cuts out pieces of tapes of desired shapes. The process can be controlled digitally via the tape converting management system 6 of FIG. 2. The cutter can be laser or blade. Means 114 for customer to easily pick up the tape pieces and/or automatically package or seal the tapes are also provided in the machine 110.

The machine 110 may further include a user interface 117 to interact with the user including, for example, receiving the user's input, presenting a tape design to the user, indicating the status of the machine, etc. The machine 110 may further include a communication device 118 communicatively connected to the cloud computing environment 130 and other devices or components of the system 100 of FIG. 1. The machine 110 may further include a processor 116 to process the instructions received from the tape converting management system 6 of FIG. 2, generate and send the corresponding control signals to the components (e.g., the roll stock, the applicators, the pattern cutter, the pickup and packaging component, etc.) of the machine to modify the tape according to the instructions.

Figure 5:
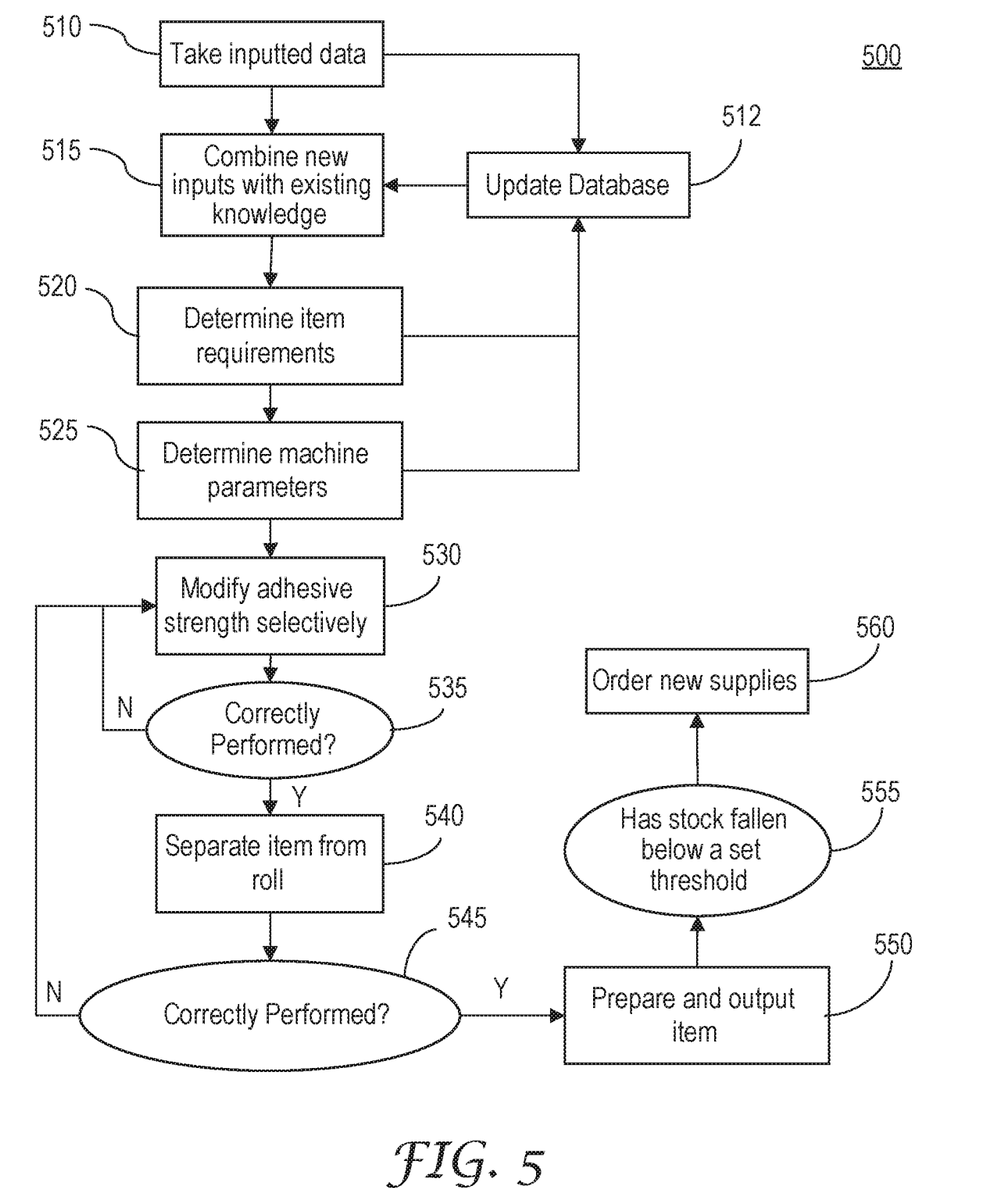
FIG. 5 is a flow diagram of a method of customizing a medical tape, according to one embodiment.

FIG. 5 is a flow diagram of a method 500 of customizing a medical tape for a user, according to one embodiment. The method 500 can be implemented via the management system 6 of FIG. 2. At 510, the system instructs to take input data from the user. The input data may include. At 520, the system combines the new input data from the user with existing knowledge from a database. At 512, the database is updated to reflect the new inputs. At 520, the system determines item requirements for the customized tape. At 525, the system determines machine parameters for a tape manufacturing core to make the customized tape. At 530, the system instructs the tape manufacturing core to selectively modify adhesive strength. At 535, the system determines whether the modification is correctly performed. When the system determines that the modification is correctly performed, the method 500 proceeds to 540 where the item is separated from the roll. When the system determines that the modification is not correctly performed, the method 500 proceeds to 530 where the system instructs the tape manufacturing core to discard the item and selectively modify adhesive strength on a new span of tape. At 545, the system determines whether the separation is correctly performed. When the system determines that the separation is correctly performed, the method 500 proceeds to 550 to prepare and output the item. When the system determines that the separation is not correctly performed, the method 500 proceeds to 530 to redo the modification on a new span of tape. At 555, the system determines whether the roll stock has fallen below a set threshold. If yes, the system sends notification to order new supplies at 560.

Unless otherwise indicated, all numbers expressing quantities or ingredients, measurement of properties and so forth used in the specification and embodiments are to be understood as being modified in all instances by the term "about." Accordingly, unless indicated to the contrary, the numerical parameters set forth in the foregoing specification and attached listing of embodiments can vary depending upon the desired properties sought to be obtained by those skilled in the art utilizing the teachings of the present disclosure. At the very least, and not as an attempt to limit the application of the doctrine of equivalents to the scope of the claimed embodiments, each numerical parameter should at least be construed in light of the number of reported significant digits and by applying ordinary rounding techniques.

Exemplary embodiments of the present disclosure may take on various modifications and alterations without departing from the spirit and scope of the present disclosure. Accordingly, it is to be understood that the embodiments of the present disclosure are not to be limited to the following described exemplary embodiments, but is to be controlled by the limitations set forth in the claims and any equivalents thereof.

Listing of Exemplary Embodiments

Exemplary embodiments are listed below. It is to be understood that any one of embodiments 1-10 and 11-15 can be combined.

Embodiment 1 is a system of making a customized medical tape comprising:
  one or more compact tape converting machines having a volume no greater than 5 $m^3$, at least one of the tape converting machines comprising a roll of tape, an adhesion modification mechanism configured to modify adhesion properties of the tape, and a communication device; and
  a computing device comprising a second communication device communicatively connected to the communication device of the at least one tape converting machine, one or more computer processors, and a non-transitory, tangible computer-readable memory comprising instructions that when executed by the one or more computer processors cause the computer processors to:
  generate for display a user interface that allows a user to input instructions to modify the adhesion properties of the tape; and
  analyze the instructions to determine machine run parameters for the one or more tape converting machines.

Embodiment 2 is the system of embodiment 1, further comprising one or more image sensors to obtain one or more digital images of an object.

Embodiment 3 is the system of embodiment 2, wherein at least one of the image sensors is provided on a mobile device, and the user interface is displayed by the mobile device to the user.

Embodiment 4 is the system of embodiment 2 or 3, wherein the one or more computer processors are further configured to analyze the digital images to determine the machine run parameters.

Embodiment 5 is the system of any one of embodiments 1-4, wherein the adhesion modification mechanism comprises an applicator configured to apply a pattern of surface adhesive modifier on an adhesive surface of the tape.

Embodiment 6 is the system of embodiment 5, wherein the applicator includes a printer.

Embodiment 7 is the system of embodiment 5 or 6, wherein the adhesion modification mechanism further comprises a curing station configured to cure the surface adhesive modifier via radiation.

Embodiment 8 is the system of any one of embodiments 1-7, wherein the tape includes a backing to support an adhesive surface, and the adhesion modification mechanism is positioned on the side of the backing, opposite the adhesive surface, and configured to modify the backing of the tape.

Embodiment 9 is the system of any one of embodiments 1-8, wherein the adhesion modification mechanism further comprises a cutter configured to cut a pattern of through holes in the tape, optionally, the cutter includes a laser, a blade, or a die.

Embodiment 10 is the system of any one of embodiments 1-9, wherein the at least one of the tape converting machines further comprises a pattern cutter downstream of the adhesion modification mechanism, configured to cut out a customized shape from the tape.

Embodiment 11 is the system of any one of embodiments 1-10, wherein the at least one of the tape converting machines further comprises a pickup and packing mechanism downstream of the pattern cutter.

Embodiment 12 is a method of customizing a medical tape, the method comprising:
  accessing to one or more compact tape converting machines having a volume no greater than 5 m$^3$, at least one of the tape converting machines comprising a roll of tape, an adhesion modification mechanism configured to modify adhesion properties of the tape, and a communication device; and
  accessing to a computing device comprising a second communication device communicatively connected to the communication device of the at least one tape converting machine, one or more computer processors, and a non-transitory, tangible computer-readable memory comprising instructions that when executed by the one or more computer processors cause the computer processors to:
  generate for display a user interface that allows a user to input instructions to modify the adhesion properties of the tape; and
  analyze the instructions to determine machine run parameters for the one or more tape converting machines.

Embodiment 13 is the method of embodiment 12, wherein the computing device is further configured to generate an automated modification configuration.

Embodiment 14 is the method of embodiment 13, further comprising presenting, via a user interface, a query including the automated modification configuration to a user.

Embodiment 15 is the method of embodiment 14, further comprising receiving a feedback from the user and modifying the automated modification configuration based on the feedback.

EXAMPLES

These examples are merely for illustrative purposes and are not meant to be limiting on the scope of the appended claims.

Example 1

Figure 6:
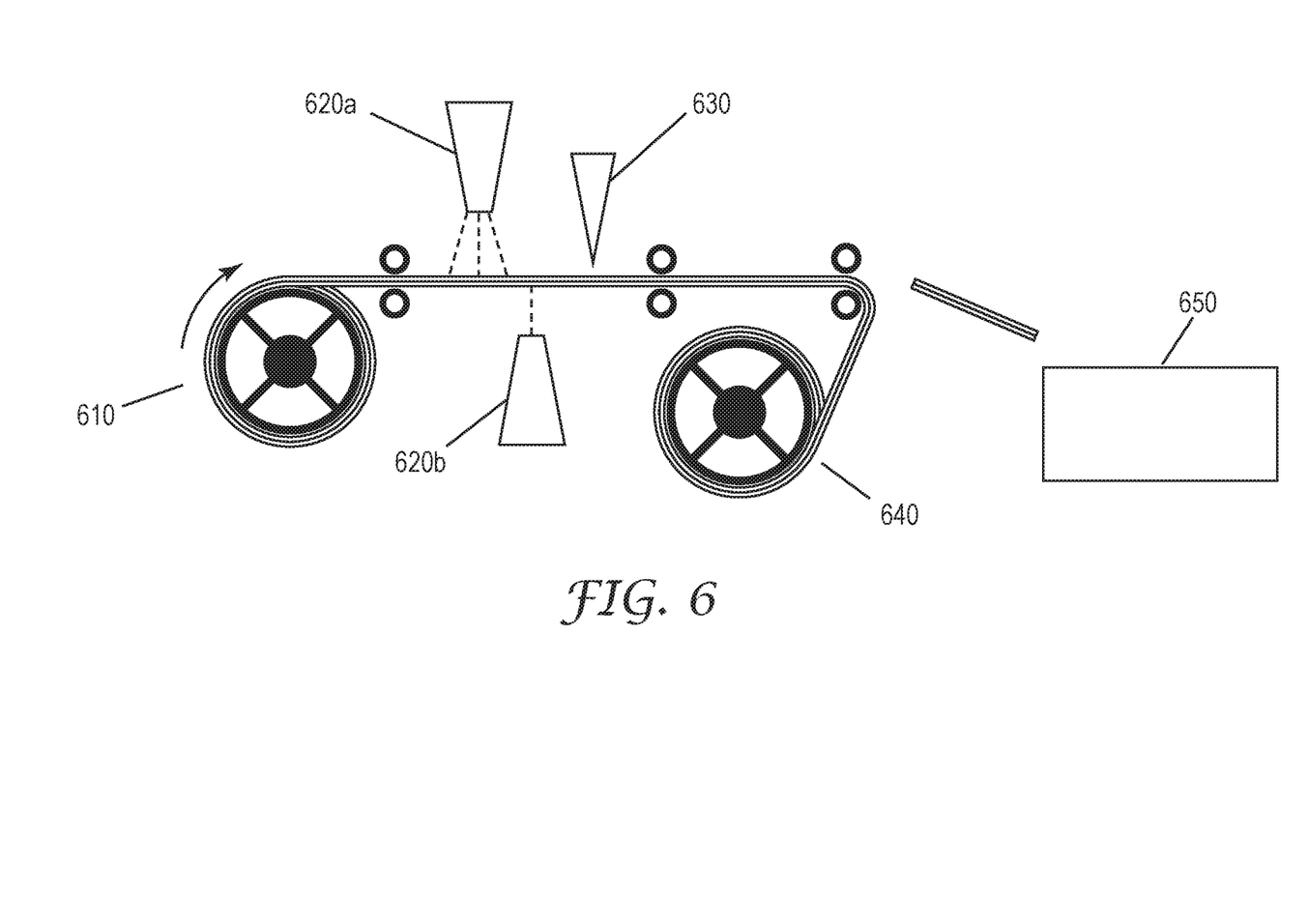
FIG. 6 illustrates a schematic diagram of a tape converting machine according to Example 1.

Example 1, depicted in FIG. 6, illustrates a basic system of an edge manufacturing core described herein. It starts with a supply roll 610 of roll stock adhesive tape of certain properties of adhesion, made in mass production. The tape passes through a series of applicators 620a, 620b that modify adhesion properties, shapes (2D), forms (3D), colors and printing information or graphics as customers and operators need, as well as package each or a few pieces of the custom tape for picking up, storage and transportation before usage. The applicator of adhesion surface modifier 620a. 620b in Example 1 is one category of modifiers that interact directly on the side of adhesive coating. The interaction of the modifier with adhesive can be physical, chemical, optical, acoustic, etc. The applicators can be, not inclusively, inkjet printheads, UV light, laser, spray jet, 3D printing. The system of the edge manufacturing core for custom tapes can also include a cutter 630 that cuts out pieces of tapes of desired shapes, also controlled digitally. The cutter 630 can be laser or blade. The backing facilitates easier handling/stacking/packaging when the cut and dispensed customized articles potentially could be of complex shapes and unwieldy sizes. The backing may contain peel tabs or other user assist features to allow the end user to easily expose the adhesive surface. In addition, the backing may also provide some rigidity or structural support for the customized adhesive article particularly if the shapes/sizes have small or intricate features. Inkjet printing 620b on the adhesive backing generate specific customized markings to aide in centering/positioning of the customized adhesive article thus removing uncertainty during application. The weeds roll 640 removes any unused stock roll material as a continuous roll of weed generated from the process. Means 650 for customer to easily pick up the tape pieces and/or automatically package or seal the tapes are also provided in the machine though not sketched extensively yet.

Example 2

Figure 7:
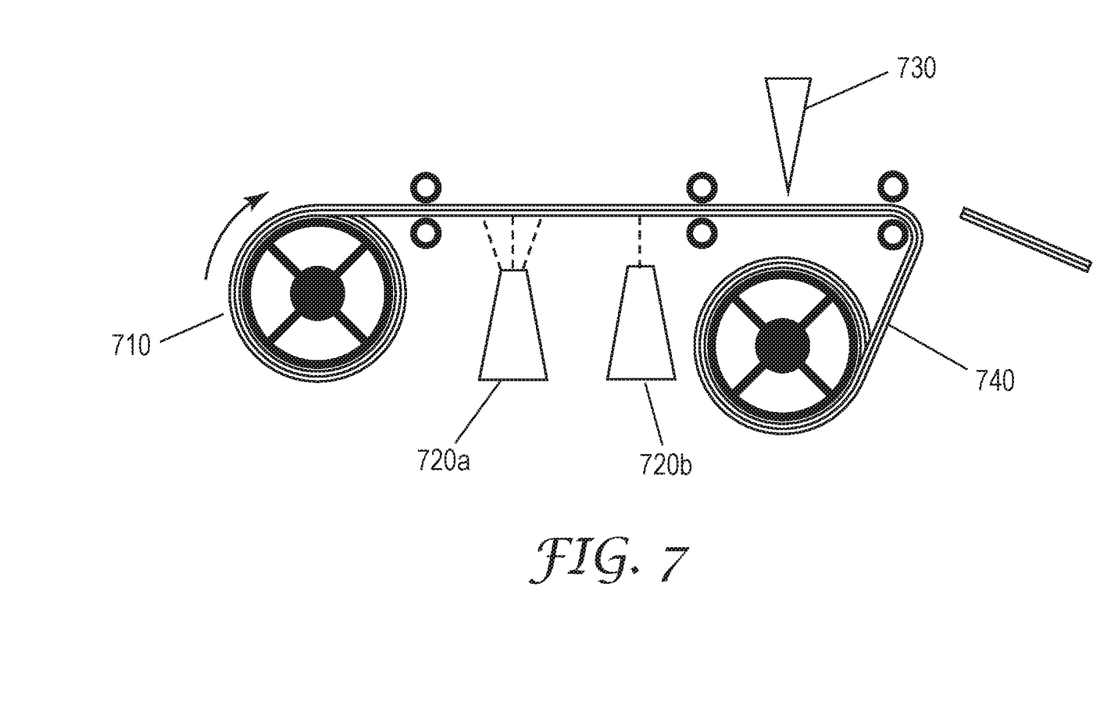
FIG. 7 illustrates a schematic diagram of a tape converting machine according to Example 2.

In Example 2, depicted in FIG. 7, a supply roll 710 of adhesive tape on a backing is provided. This porous/transparent backing functions to a) allow the penetrating adhesive modifier 720a to act across it, b) prevent the adhesive of the tape from being contaminated before/during/after the adhesive is being modified, and c) facilitate easier handling/stacking/packaging when the cut and dispensed customized articles potentially could be of complex shapes and unwieldy sizes. The backing may contain peel tabs or other user assist features to allow the end user to easily expose the adhesive surface. In addition, the backing may also provide some rigidity or structural support for the customized adhesive article particularly if the shapes/sizes have small or intricate features. Inkjet printing 720b on the adhesive backing generate specific customized markings to aide in centering/positioning of the customized adhesive article thus removing uncertainty during application. A pattern cutter 730 subsequently trims the modified adhesive tape to the desired size/shape. The weeds roll 740 removes any unused stock roll material as a continuous roll of weed generated from the process.

Example 3

Figure 8:
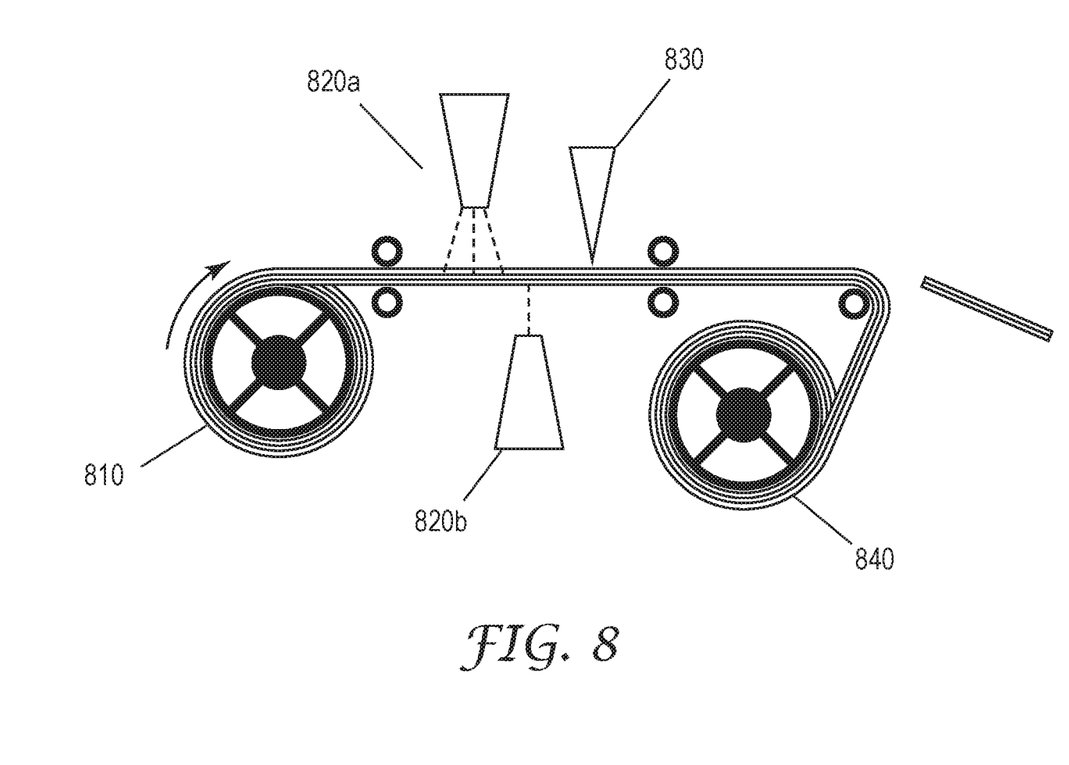
FIG. 8 illustrates a schematic diagram of a tape converting machine according to Example 3.

In Example 3, depicted in FIG. 8, a supply roll 810 of adhesive tape on a backing is provided with an integral porous/transparent liner. This porous/transparent liner functions to a) allow the penetrating adhesive modifier 820a to act across it, b) prevent the adhesive of the tape from being contaminated before/during/after the adhesive is being modified, and c) facilitate easier handling/stacking/packaging when the cut and dispensed customized articles potentially could be of complex shapes and unwieldy sizes. The liner may contain peel tabs or other user assist features to allow the end user to easily expose the adhesive surface. In addition, the liner may also provide some rigidity or structural support for the customized adhesive article particularly if the shapes/sizes have small or intricate features. Inkjet printing 820b on the adhesive backing generate specific customized markings to aide in centering/positioning of the customized adhesive article thus removing uncertainty during application. A pattern cutter 830 subsequently trims the modified adhesive tape to the desired size/shape. The takeup roll 840 removes any unused stock roll material as a continuous roll of weed generated from the process.

Example 4

Figure 9:
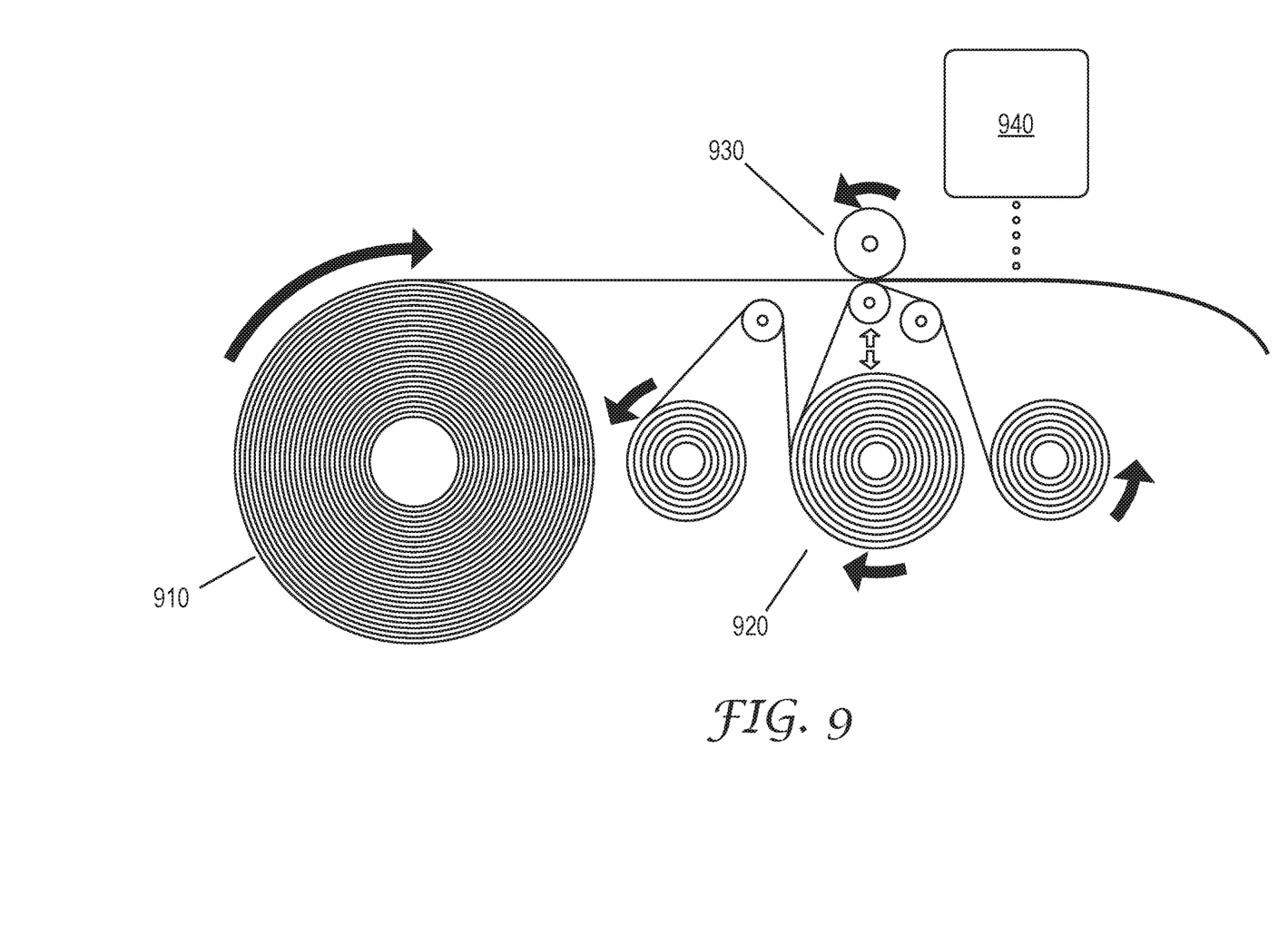
FIG. 9 illustrates a schematic diagram of a tape converting machine according to Example 4.

In Example 4, depicted in FIG. 9, a continuously customizable adhesive tape being generated via a lamination process with two adhesive rolls and a printer is shown. A feed roll 910, commercially available from 3M Company (St. Paul, MN) under the tradename Micropore, is depicted threading through the machine. An emblem adhesive 920, commercially available from 3M Company (St. Paul, MN) under the tradename Press-In-Place, possessing spaced-apart adhesive regions/dots interspersed between two liners are introduced to the Micropore adhesive surface. This lamination process is discontinuous in that these adhesive dots only transfer to the Micropore adhesive surface when a roller is actuated to act against the pressure roll 930. The roller acting against the pressure roll 930 essentially introduces the adhesive dots to be bonded to the Micropore adhesive surface. A printer 940 is depicted to act on the backing of the Micropore tape. A cut-off mechanism (not shown) subsequently trims the customized Micropore tape to the desired size/shape. While this graphic depicts alteration/modification along the length dimension of the Micropore tape, as an extension, similar modifications may occur across the width of the Micropore tape as well with replicated Press-In-Place Emblem Adhesive transfer mechanisms.

Reference throughout this specification to "one embodiment," "certain embodiments," "one or more embodiments," or "an embodiment," whether or not including the term "exemplary" preceding the term "embodiment," means that a particular feature, structure, material, or characteristic described in connection with the embodiment is included in at least one embodiment of the certain exemplary embodiments of the present disclosure. Thus, the appearances of the phrases such as "in one or more embodiments," "in certain embodiments," "in one embodiment," or "in an embodiment" in various places throughout this specification are not necessarily referring to the same embodiment of the certain exemplary embodiments of the present disclosure. Furthermore, the particular features, structures, materials, or characteristics may be combined in any suitable manner in one or more embodiments.

While the specification has described in detail certain exemplary embodiments, it will be appreciated that those skilled in the art, upon attaining an understanding of the foregoing, may readily conceive of alterations to, variations of, and equivalents to these embodiments. Accordingly, it should be understood that this disclosure is not to be unduly limited to the illustrative embodiments set forth hereinabove. In particular, as used herein, the recitation of numerical ranges by endpoints is intended to include all numbers subsumed within that range (e.g., 1 to 5 includes 1, 1.5, 2, 2.75, 3, 3.80, 4, and 5). In addition, all numbers used herein are assumed to be modified by the term "about." Furthermore, various exemplary embodiments have been described. These and other embodiments are within the scope of the following claims.

What is claimed is:

1. A system for making a customized medical tape, the system comprising:
one or more compact tape converting machines having a volume no greater than 5 m$^3$, at least one of the tape converting machines comprising a roll of medical tape, an adhesion modification mechanism configured to modify adhesion properties of the medical tape, and a communication device; and
a computing device comprising a second communication device communicatively connected to the communication device of the at least one tape converting machine, one or more computer processors, and a non-transitory, tangible computer-readable memory comprising instructions that when executed by the one or more computer processors cause the computer processors to:
generate, for display, a user interface,
receive, via the user interface, one or more input instructions to modify the adhesion properties of the tape;
analyze the instructions to determine machine run parameters for the one or more tape converting machines;
apply the machine run parameters to determine a first adhesion property with respect to a first area of a single strip of the roll of medical tape and a second adhesion property that is different from the first adhesion property with respect to a second area of the single strip of the roll of medical tape; and
cause the at least one tape converting machine to modify the adhesion properties such that the single strip of the roll of medical tape has the first adhesion property at the first area and the second adhesion property at the second area.

2. The system of claim 1, further comprising one or more image sensors to obtain one or more digital images of an object.

3. The system of claim 2, wherein at least one of the image sensors is provided on a mobile device, and the user interface is displayed by the mobile device to the user.

4. The system of claim 2, wherein the one or more computer processors are further configured to analyze the digital images to determine the machine run parameters.

5. The system of claim 1, wherein the adhesion modification mechanism comprises an applicator configured to apply a pattern of surface adhesive modifier on an adhesive surface of the single strip of the roll of medical tape.

6. The system of claim 5, wherein the applicator includes a printer.

7. The system of claim 5, wherein the adhesion modification mechanism further comprises a curing station configured to cure the surface adhesive modifier via radiation.

8. The system of claim 5, wherein the first and second adhesion properties are based on different target areas on a patient with respect to the first and second areas of the single strip of the roll of medical tape.

9. The system of claim 1, wherein the medical tape includes a backing to support an adhesive surface, and wherein the adhesion modification mechanism is positioned on the side of the backing, opposite the adhesive surface, and configured to modify the backing of the medical tape.

10. The system of claim 1, wherein the adhesion modification mechanism further comprises a cutter configured to cut a pattern of through holes in the tape, optionally, the cutter includes a laser, a blade, or a die.

11. The system of claim 1, wherein the at least one of the tape converting machines further comprises a pattern cutter downstream of the adhesion modification mechanism, configured to cut out the single strip according to a customized shape from the roll of medical tape.

12. The system of claim 1, wherein the at least one of the tape converting machines further comprises a pickup and packing mechanism positioned downstream of the pattern cutter.

13. A method of customizing medical tape, the method comprising:

accessing one or more compact tape converting machines having a volume no greater than 5 m³, at least one of the tape converting machines comprising a roll of the medical tape, an adhesion modification mechanism configured to modify adhesion properties of the medical tape tape, and a communication device; and accessing a computing device comprising a second communication device communicatively connected to the communication device of the at least one tape converting machine, one or more computer processors, and a non-transitory, tangible computer-readable memory comprising instructions that when executed by the one or more computer processors cause the computer processors to:

generate, for display, a user interface that allows a user to input instructions to modify the adhesion properties of the tape;

analyze the instructions to determine machine run parameters for the one or more tape converting machines apply the machine run parameters to determine a first adhesion property with respect to a first area of a single strip of the roll of medical tape and a second adhesion property that is different from the first adhesion property with respect to a second area of the single strip of the roll of medical tape; and cause the at least one tape converting machine to modify the adhesion properties such that the single strip of the roll of medical tape has the first adhesion property at the first area and the second adhesion property at the second area.

14. The method of claim 13, wherein the computing device is further configured to generate an automated modification configuration.

15. The method of claim 14, further comprising presenting, via the user interface, a query including the automated modification configuration to a user.

16. The method of claim 15, further comprising:
receiving feedback from the user; and
modifying the automated modification configuration based on the feedback.

* * * * *

UNITED STATES PATENT AND TRADEMARK OFFICE
CERTIFICATE OF CORRECTION

| | |
|---|---|
| PATENT NO. | : 12,346,547 B2 |
| APPLICATION NO. | : 18/717723 |
| DATED | : July 1, 2025 |
| INVENTOR(S) | : Md Abdulla Al Masud et al. |

Page 1 of 1

It is certified that error appears in the above-identified patent and that said Letters Patent is hereby corrected as shown below:

In the Claims

<u>Column 13</u>
Line 5-6, In Claim 13, delete "medical tape tape" and insert -- medical tape --, therefor.

Signed and Sealed this
Tenth Day of February, 2026

John A. Squires
*Director of the United States Patent and Trademark Office*